(12) United States Patent
Wu et al.

(10) Patent No.: US 10,786,280 B2
(45) Date of Patent: Sep. 29, 2020

(54) TROCAR

(71) Applicants: MEGAFORCE COMPANY LIMITED, New Taipei (TW); COREBIO TECHNOLOGIES CO., LTD., Taoyuan (TW)

(72) Inventors: Fu-Po Wu, New Taipei (TW); Kai-Ping Wang, New Taipei (TW); Chih-Hao Chen, Taoyuan (TW)

(73) Assignees: MEGAFORCE COMPANY LIMITED, New Taipei (TW); COREBIO TECHNOLOGIES CO., LTD., Taoyuan (TW)

( * ) Notice: Subject to any disclaimer, the term of this patent is extended or adjusted under 35 U.S.C. 154(b) by 367 days.

(21) Appl. No.: 15/944,552

(22) Filed: Apr. 3, 2018

(65) Prior Publication Data
US 2019/0150982 A1 May 23, 2019

(30) Foreign Application Priority Data
Nov. 17, 2017 (CN) .......................... 2017 1 1142244

(51) Int. Cl.
*A61B 17/34* (2006.01)
*A61M 13/00* (2006.01)
*A61B 17/00* (2006.01)

(52) U.S. Cl.
CPC ...... *A61B 17/3496* (2013.01); *A61B 17/3417* (2013.01); *A61B 17/3421* (2013.01); *A61B 17/00234* (2013.01); *A61B 2017/3443* (2013.01); *A61B 2017/3486* (2013.01); *A61M 13/00* (2013.01)

(58) Field of Classification Search
CPC ............ A61B 17/3496; A61B 17/3417; A61B 17/3421; A61B 17/00234; A61M 13/00
See application file for complete search history.

(56) References Cited

U.S. PATENT DOCUMENTS

| | | | | |
|---|---|---|---|---|
| 5,176,697 A * | 1/1993 | Hasson | ................. | A61B 17/34 604/174 |
| 6,197,002 B1 * | 3/2001 | Peterson | ............ | A61B 17/3417 604/164.01 |
| 6,908,454 B2 * | 6/2005 | McFarlane | ......... | A61B 17/3421 604/104 |

(Continued)

*Primary Examiner* — Laura A Bouchelle
*Assistant Examiner* — Justin L Zamory
(74) *Attorney, Agent, or Firm* — Muncy, Geissler, Olds & Lowe, P.C.

(57) ABSTRACT

A trocar includes a puncturing device and a sleeving component. The puncturing device includes a base and a puncturing portion. The puncturing portion includes a bump and a tip. The bump extends from an outer surface of the puncturing portion radially. The sleeving component includes a gas pressure base, a first tube assembly, a second tube assembly, and a fixation base. The second tube assembly is retractable. The fixation base is fixed to the second sleeving end and includes a guiding groove and a key groove. The guiding groove communicates the key groove. While the bump of the puncturing device is entered through the guiding groove, and the puncturing device is rotated to have the bump be in the key groove, the puncturing device is secured to the fixation base, and the puncturing device drives the fixation base to move along an elongated direction of the puncturing device.

10 Claims, 8 Drawing Sheets

(56) References Cited

U.S. PATENT DOCUMENTS

| | | | | |
|---|---|---|---|---|
| 7,384,423 | B1 * | 6/2008 | Chin | A61B 17/00008 |
| | | | | 606/190 |
| 8,409,085 | B2 * | 4/2013 | Lozman | A61B 17/1684 |
| | | | | 600/204 |
| 2002/0026207 | A1 * | 2/2002 | Stellon | A61B 17/3496 |
| | | | | 606/185 |
| 2005/0004592 | A1 * | 1/2005 | Criscuolo | A61B 17/0218 |
| | | | | 606/190 |
| 2005/0165432 | A1 * | 7/2005 | Heinrich | A61B 17/3417 |
| | | | | 606/167 |
| 2006/0025749 | A1 * | 2/2006 | Moenning | A61M 39/02 |
| | | | | 604/506 |
| 2011/0152788 | A1 * | 6/2011 | Hotter | A61B 17/3498 |
| | | | | 604/256 |
| 2015/0038793 | A1 * | 2/2015 | Prior | A61B 17/0482 |
| | | | | 600/204 |
| 2018/0153537 | A1 * | 6/2018 | Wang | A61M 13/00 |

* cited by examiner

TROCAR

CROSS-REFERENCE TO RELATED APPLICATION

This non-provisional application claims priority under 35 U.S.C. § 119(a) to Patent Application No. 201711142244.3 filed in China, P.R.C. on Nov. 17, 2017, the entire contents of which are hereby incorporated by reference.

BACKGROUND

Technical Field

The instant disclosure relates to a minimally invasive surgery tool and, more particularly, to a trocar.

Related Art

Nowadays, a surgical knife can be replaced by a trocar for a surgical operation. The trocar can be used to cut an opening on a human body. Further, medical devices such as an optical fiber, an endoscope, or a laser tool can be used to perform an operation such as burning or removing. By such manner of surgery, a wound on a patient may be minimized, the feel of pain for a patient may be eased, time for bedridden and rest after a patient have an operation may be shorten, and a scar on a patient may be reduced. Because such kind of surgery results in small wounds and quick recoveries on patients, it is also known as a minimally invasive surgery.

The trocar usually includes a long tube and a puncturing tool. The puncturing tool is inserted into the long tube. After the puncturing tool is used to cut an opening on a human body or an animal body, the puncturing tool can be retrieved from the long tube. The long tube would be secured onto the human body, and then a relative surgical tool such as an optical fiber, an endoscope, or a laser tool can be moved into the human body deeply through the long tube to perform an operation such as burning or removing tissues.

During an operation, the long tube would be secured onto a human body or an animal body; however, the length of a conventional long tube of a trocar is too long, so that the long tube is easy to be touched and swayed unintentionally. This could be a disturbance to the surgical staff. In addition, a tool may shift related to the long tube since the tool is merely restricted by the wall of the long tube. If the tool shifts from a predetermined position and is required to be adjusted, the adjustment of the tool may cause an unnecessary damage and make a wound enlarged. The patient may be in pain and feel uncomfortable.

SUMMARY

To address the above issue, the instant disclosure provides a trocar. The trocar comprises a puncturing device and a sleeving component. The puncturing device comprises a base and a puncturing portion. The puncturing portion extends along a direction perpendicular to the base. The puncturing portion comprises a bump and a tip. The tip is on an end of the puncturing portion opposite to the base. The bump extends from an outer surface of the puncturing portion radially. The sleeving component comprises a gas pressure base, a first tube assembly, a second tube assembly, a fixation base, and a gas cell.

The gas pressure base comprises a handle, a connecting portion, and a first gas valve. The handle comprises an opening. The puncturing portion is inserted into the opening. The base contacts the handle. The connecting portion extends from the handle and comprises an assembling channel. The assembling channel communicates with the opening. The first gas valve is connected with the connecting portion and communicates with the assembling channel. The first tube assembly comprises a first assembling end and a first sleeving end. The first assembling end is assembled into the assembling channel. The first assembling end is corresponding to the first gas valve. A wall of the first sleeving end comprises at least one first opening. The second tube assembly comprises a second assembling end and a second sleeving end. The second assembling end is adjustably sleeved to the first sleeving end. The second tube assembly is retractable relative to the first tube assembly to have the first tube assembly received in the second tube assembly. Therefore, a total length of the first tube assembly and the second tube assembly is reduced. The fixation base is fixed to the second sleeving end and comprises a passage, an inner wall, a guiding groove, a key groove, and a gas outlet. The passage penetrates through the fixation base. The inner wall extends from an inner surface of the fixation base towards the passage. The guiding groove communicates the passage and is adjacent to the inner wall. The key groove is on the inner wall and communicates with the guiding groove. A width of an end of the key groove away from the guiding groove is less than that of an end of the key groove close to the guiding groove. The gas outlet is on an outer surface of the fixation base. The puncturing portion is in the assembling channel, the first tube assembly, the second tube assembly, and the passage. The tip is convex on the fixation base. The gas cell is sleeved to the fixation base and is corresponding to the gas outlet. While the bump of the puncturing device is entered through the guiding groove, and the puncturing device is rotated to have the bump slide along the key groove until the bump contacts the inner wall to have the puncturing device secured to the fixation base, the puncturing device drives the sleeving component to move along an elongated direction of the puncturing device.

In some embodiments, the first tube assembly further comprises a first inner tube and a first outer tube. The first tube assembly is divided into a first wall region and a second wall region. The first outer tube is around the first inner tube in the first wall region. The first outer tube is not around the first inner tube in the second wall region. The second tube assembly comprises a second inner tube and a second outer tube. The second tube assembly is divided into a third wall region and a fourth wall region. The second outer tube is around the first outer tube in the third wall region. The second outer tube is around the second inner tube in the fourth wall region. The first opening is on a wall of the first outer tube.

Further, a gas channel is formed by a communication between the first inner tube and the first outer tube, a communication between the first opening, the first outer tube, and the second outer tube, and a communication between the second outer tube and the second inner tube, and by the gas outlet. While a gas flows into the first gas valve, the gas flows along the gas channel and into the gas cell through the gas outlet.

In some embodiments, the trocar further comprises a gas tight assembly. The gas tight assembly is disposed on a portion of the first tube assembly and a portion of the second tube assembly. The gas tight assembly seals a sleeving area of the first tube assembly and the second tube assembly. In particular, the gas tight assembly comprises a blocking component and a gas tight tube. The blocking component is assembled to the first tube assembly and is adjacent to the first sleeving end. The gas tight tube is sleeved to the sleeving area of the first tube assembly and the second tube assembly. The gas tight tube covers the blocking component.

While the trocar is extruded, the second tube assembly is moved away from the gas pressure base relative to the first tube assembly until the blocking component contacts the second tube assembly. While the sleeving component is retracted, the second tube assembly is moved towards the handle relative to the first tube assembly, and the first tube assembly is retracted in the second tube assembly until the gas tight assembly contacts the connecting portion.

Further, the gas tight assembly further comprises a gas tight ring. The gas tight ring is sleeved to a portion of the first tube assembly and contacts the blocking component. The gas tight ring is covered by the gas tight tube. In another embodiment, the gas tight assembly further comprises a securing component. The securing component is assembled to the first sleeving end and contacts an inner surface of the second inner tube.

In some embodiments, while the bump is back to the guiding groove from the key groove, the puncturing device is free to be withdrawn from the sleeving component.

According to the trocar of the embodiments of the instant disclosure, the puncturing device can be secured to the fixation base of the sleeving component by the bump and the key groove. Therefore, the puncturing device can be moved with the sleeving component along an axial direction synchronously so as to be adjusted to a proper position. In addition, the first tube assembly and the second tube assembly are sleeved to each other, and the first tube assembly can be received in the second tube assembly such that a length of the sleeving component can be adjusted. Whether the sleeving component is in an extruded state or in a retracted state, the puncturing device can be moved with the sleeving component synchronously and is easy to be adjusted immediately, which can avoid unnecessary damage and prevent wounds from being enlarged by unintentional contact. Patient can have less pain and less uncomfortable feeling. A length of a portion of the sleeving component outside a human body can be shorten, which is convenient to medical staff for performing an operation.

DETAILED DESCRIPTION

Figure 1:
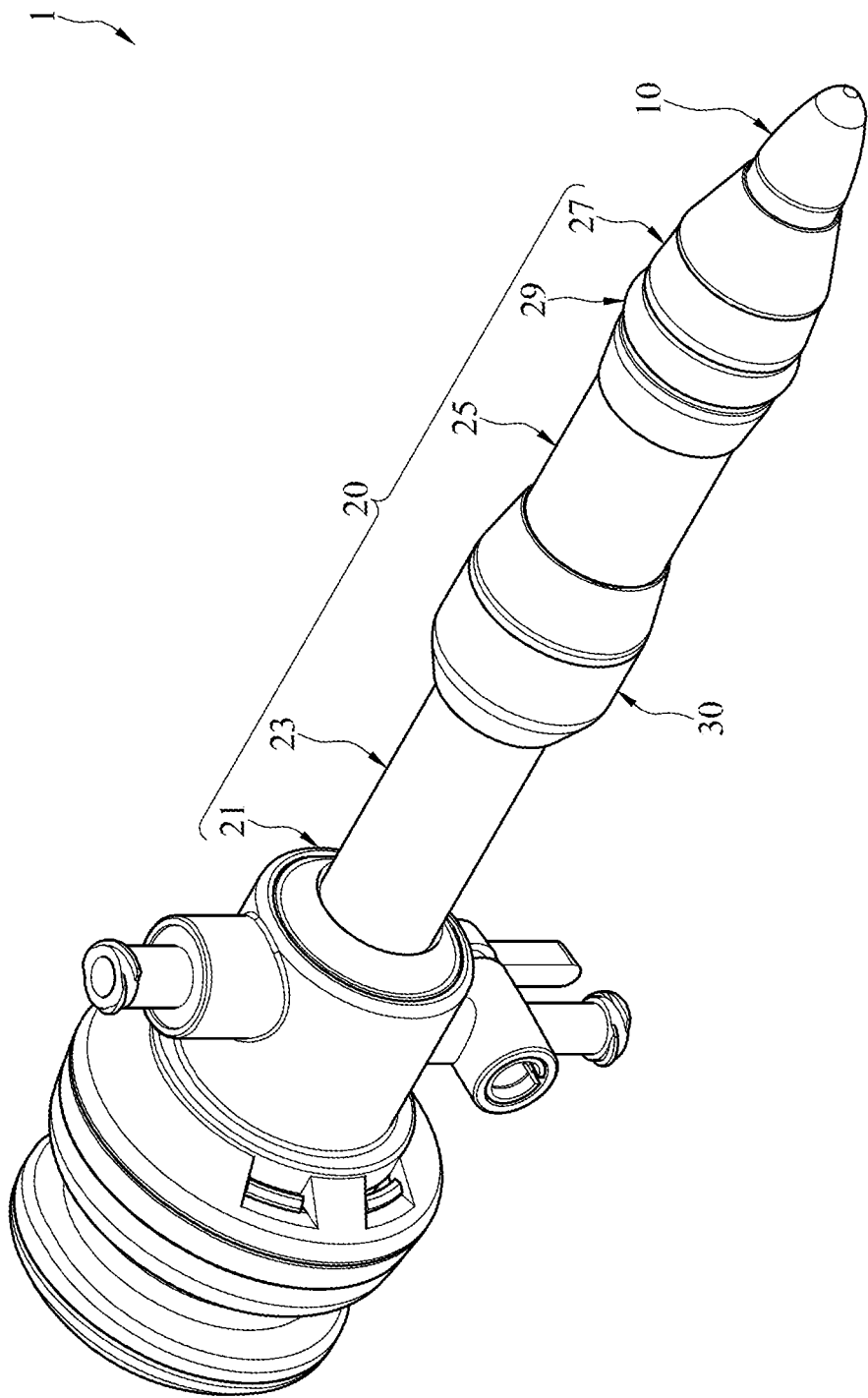
FIG. 1 illustrates a perspective view of a trocar according to an embodiment of the instant disclosure.
Figure 2:
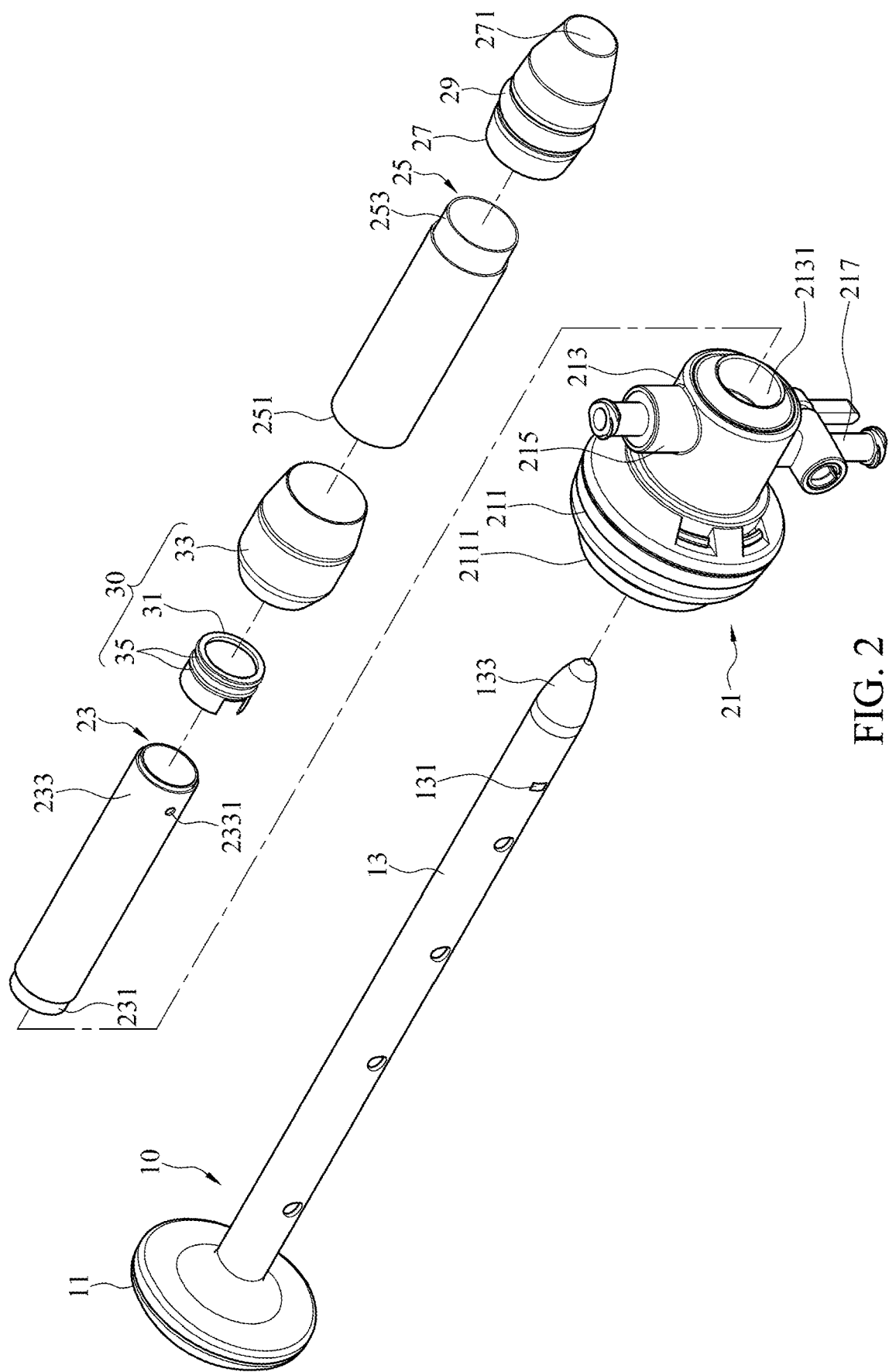
FIG. 2 illustrates an exploded view of a trocar according to an embodiment of the instant disclosure.
Figure 3:
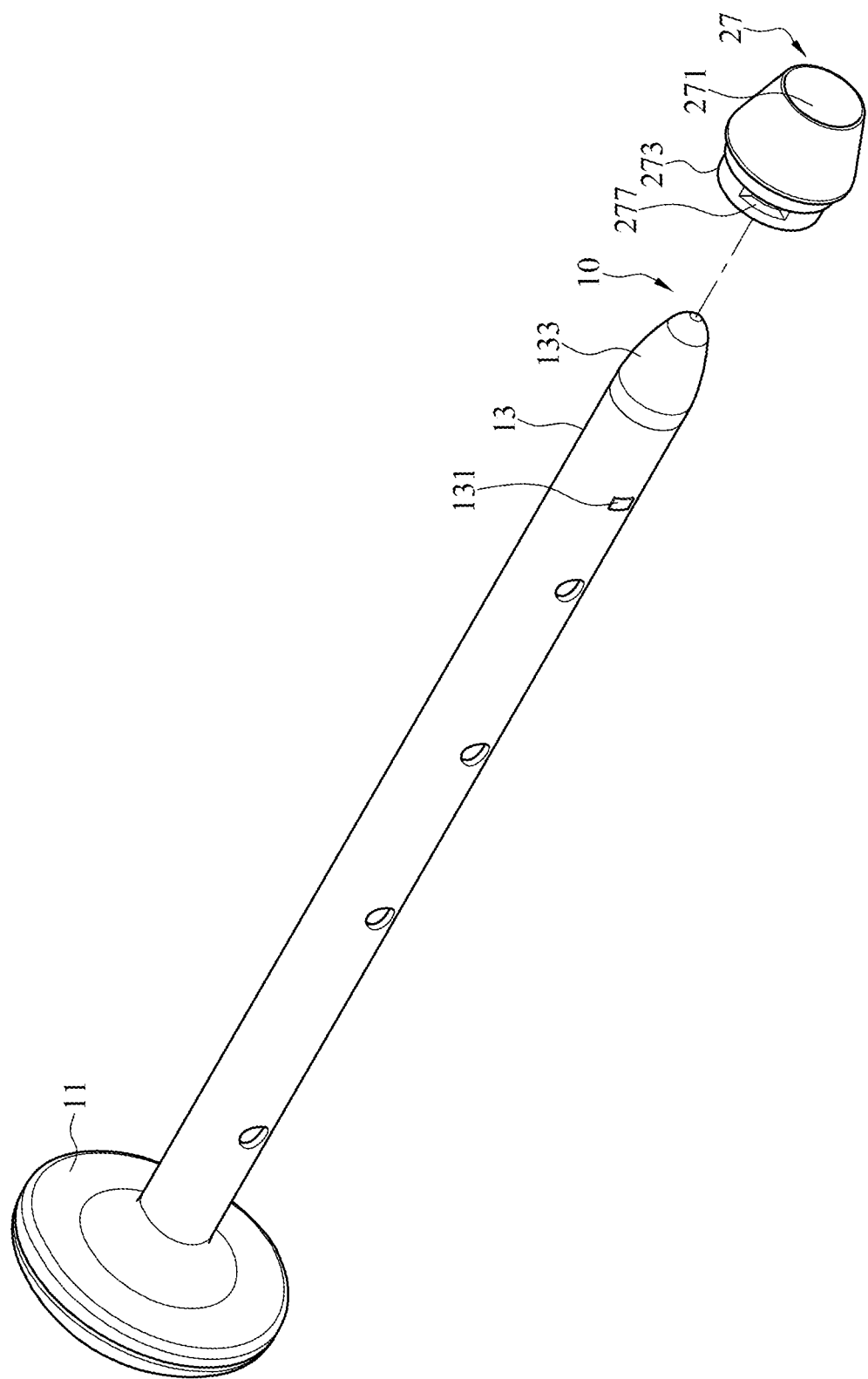
FIG. 3 illustrates a partially enlarged view of a fixation base and a puncturing device of FIG. 2.
Figure 3A:
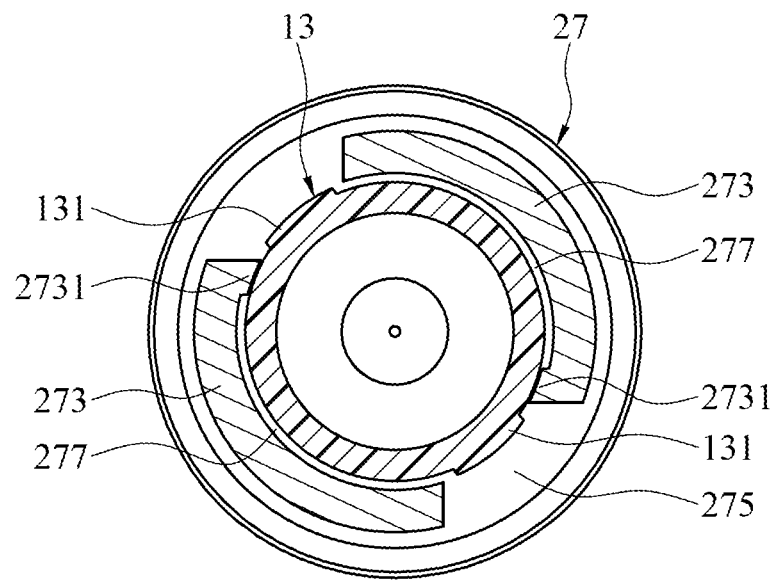
FIG. 3A illustrates a cross-sectional view of the puncturing device of FIG. 3 not secured to the fixation base.
Figure 3B:
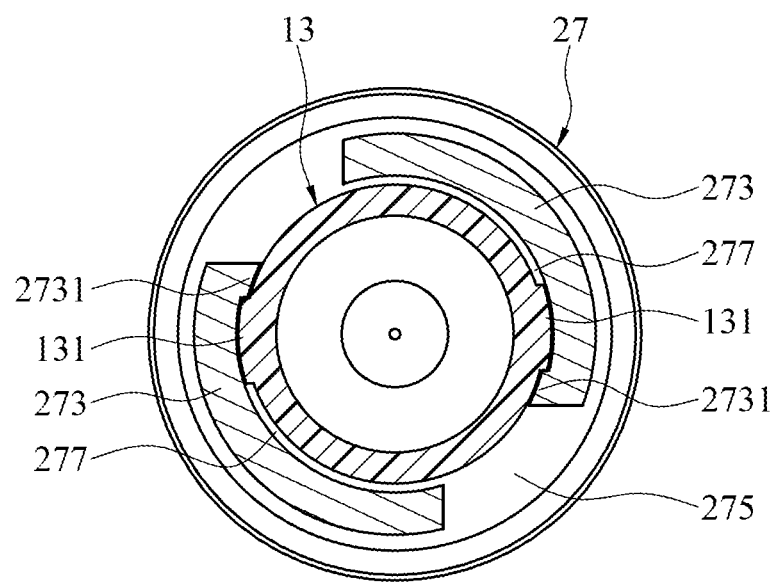
FIG. 3B illustrates a cross-sectional view of the puncturing device of FIG. 3 secured to the fixation base.
Figure 4:
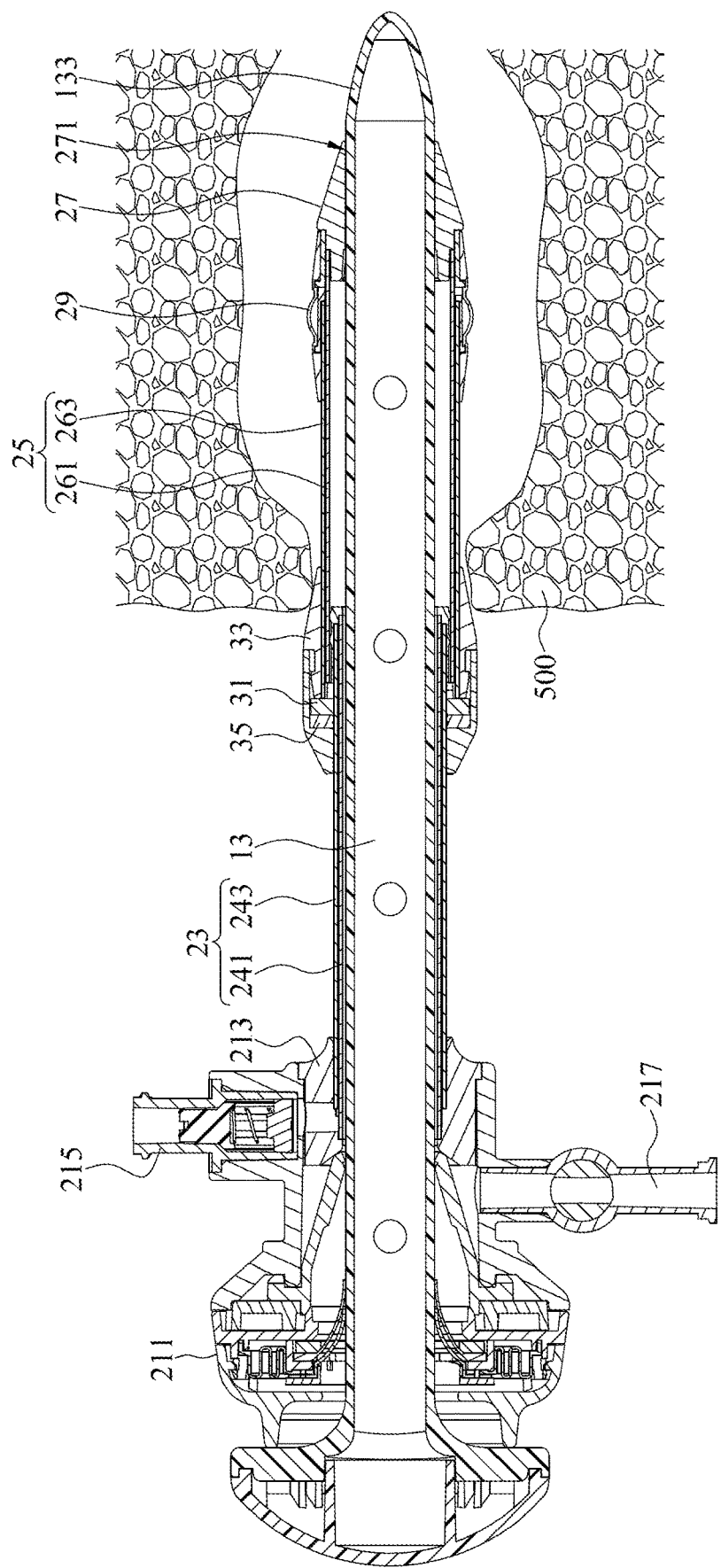
FIG. 4 illustrates a cross-sectional view of a trocar in an operation according to an embodiment of the instant disclosure.
Figure 5:
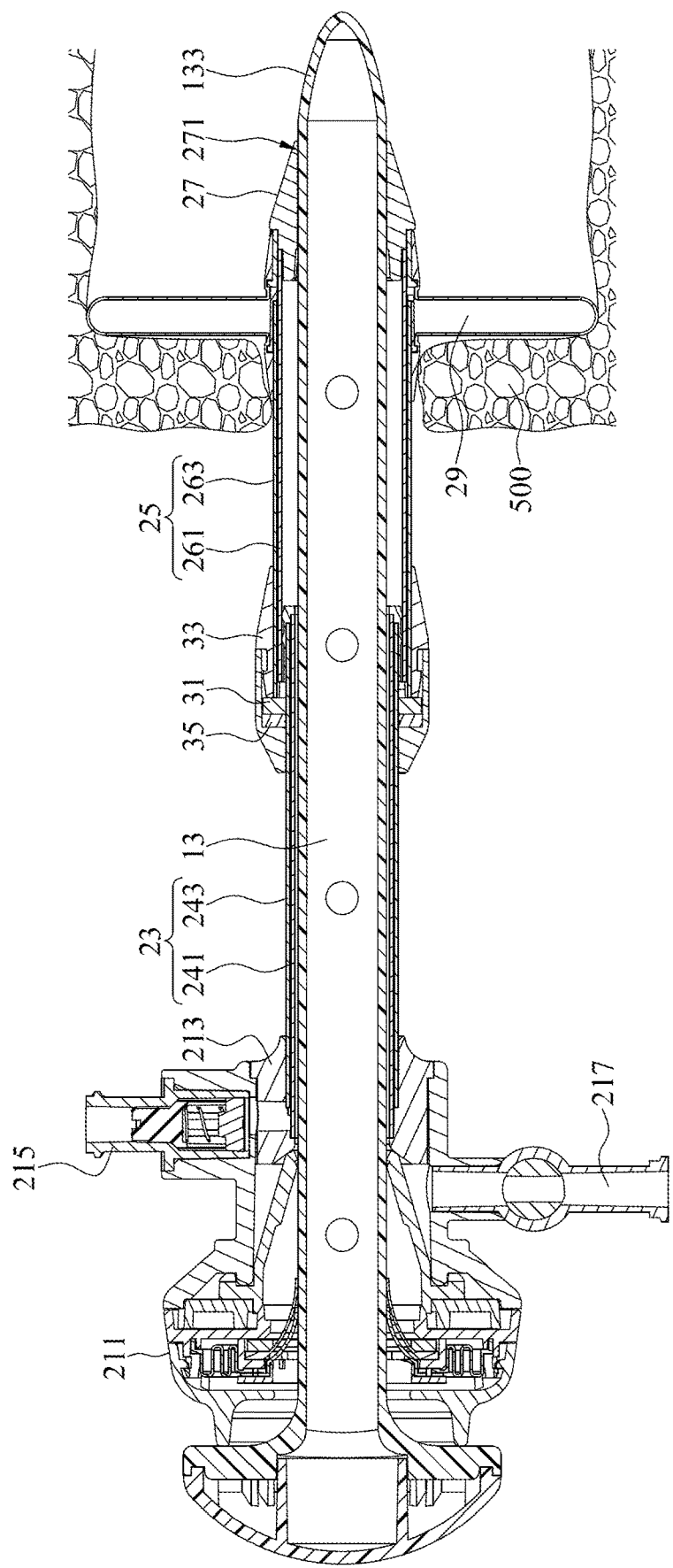
FIG. 5 illustrates a cross-sectional view of a trocar moved and positioned along an axial direction according to an embodiment of the instant disclosure.
Figure 6:
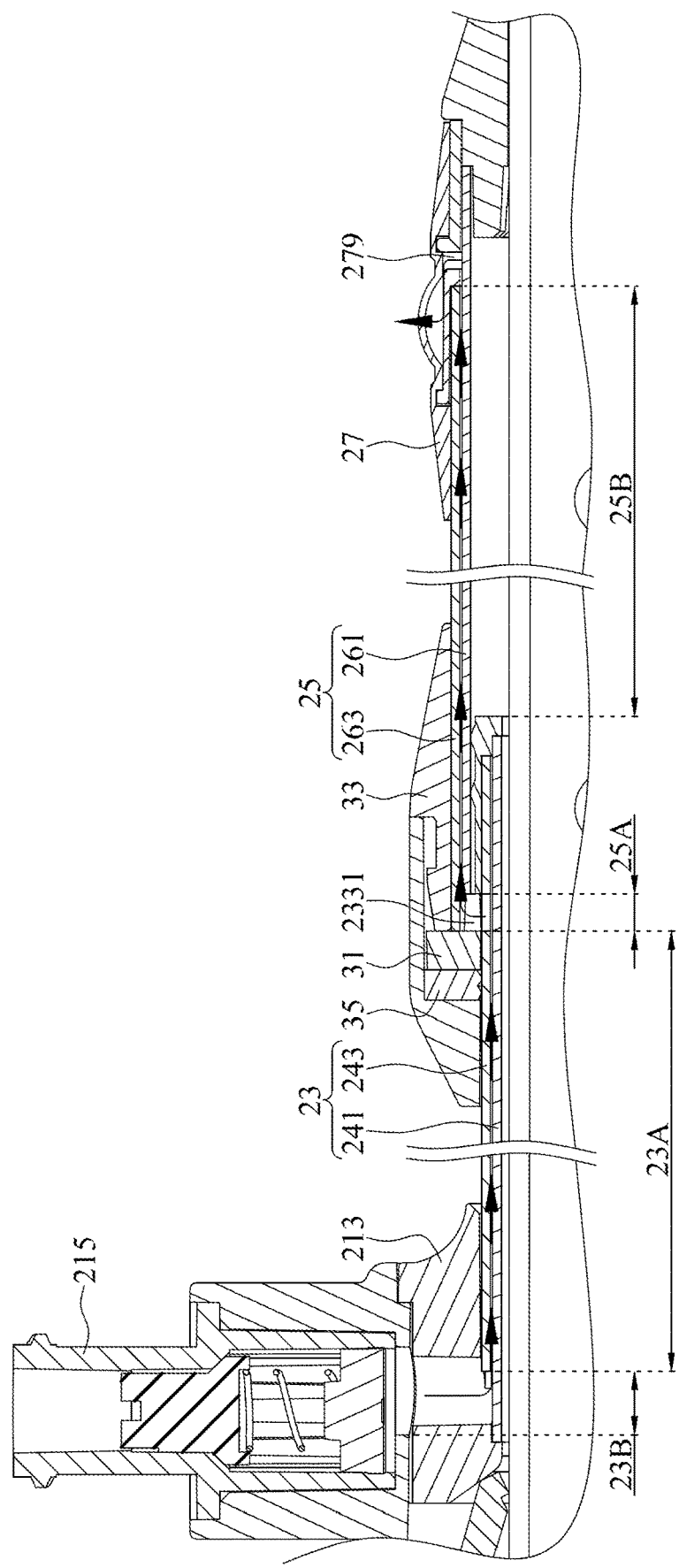
FIG. 6 illustrates a partially cross-sectional view of a sleeving component of FIG. 5.
Figure 7:
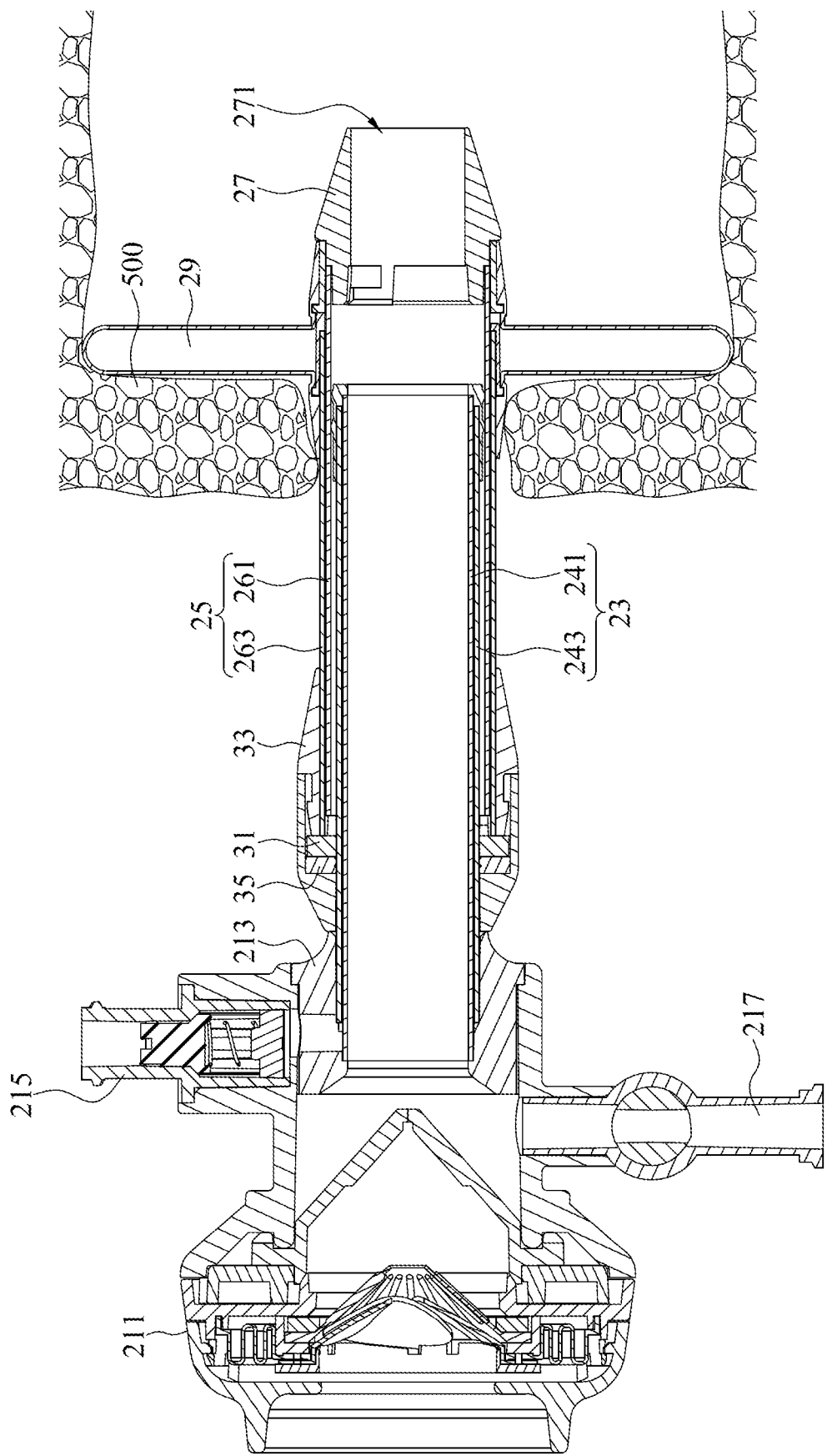
FIG. 7 illustrates a cross-sectional view of the sleeving component of FIG. 5 in a retracted state.

FIG. 1 and FIG. 2 are respectively a perspective view of a trocar according to an embodiment of the instant disclosure and an exploded view of a trocar according to an embodiment of the instant disclosure. FIG. 3 is a partially enlarged view of a fixation base and a puncturing device of FIG. 2. FIG. 3A is a cross-sectional view of the puncturing device of FIG. 3 not secured to the fixation base. FIG. 3B is a cross-sectional view of the puncturing device of FIG. 3 secured to the fixation base. FIG. 4 is a cross-sectional view of a trocar in an operation according to an embodiment of the instant disclosure. FIG. 5 is a cross-sectional view of a trocar moved and positioned along an axial direction according to an embodiment of the instant disclosure. FIG. 6 is a partially cross-sectional view of a sleeving component of FIG. 5. FIG. 7 is a cross-sectional view of the sleeving component of FIG. 5 in a retracted state.

As shown in FIG. 1 and FIG. 2, the trocar 1 comprises a puncturing device 10 and a sleeving component 20. The puncturing device 10 comprises a base 11 and a puncturing portion 13. The puncturing portion 13 extends along a direction perpendicular to the base 11. The puncturing portion 13 comprises a bump 131 and a tip 133. The tip 133 is on an end of the puncturing portion 13 opposite to the base 11. The bump 131 extends from an outer surface of the puncturing portion 13 outwardly and radially. In the embodiment, the bump 131 is, but is not limited to, a radial convex bump on a part of the outer surface of the puncturing portion 13. In another embodiment, the bump 131 may be a radial, annular convex bump around the outer surface of the puncturing portion 13. The sleeving component 20 comprises a gas pressure base 21, a first tube assembly 23, a second tube assembly 25, a fixation base 27, and a gas cell 29.

As shown in FIG. 2, the gas pressure base 21 comprises a handle 211, a connecting portion 213, and a first gas valve 215. The handle 211 comprises an opening 2111. The puncturing portion 13 is inserted through the opening 2111. The base 11 contacts the handle 211. The connecting portion 213 extends from the handle 211. An extending direction of the connecting portion 213 is parallel with an elongated direction of the puncturing portion 13. The connecting portion 213 comprises an assembling channel 2131. The assembling channel 2131 communicates with the opening 2111. The first gas valve 215 is connected with the connecting portion 213 and communicates with the assembling channel 2131, such that gas flowing through the first gas valve 215 can flow into the assembling channel 2131.

The first tube assembly 23 comprises a first assembling end 231 and a first sleeving end 233. The first assembling end 231 is assembled into the assembling channel 2131. The first assembling end 231 is corresponding to the first gas valve 215. A wall of the first sleeving end 233 comprises at least one first opening 2331. The second tube assembly 25 comprises a second assembling end 251 and a second sleeving end 253. A bore of the second tube assembly 25 is greater than a bore of the first tube assembly 23. Therefore, the second assembling end 251 is adjustably sleeved to the first sleeving end 233. The second tube assembly 25 is retractable relative to the first tube assembly 23 to have the first tube assembly 23 received in the second tube assembly 25. As a result, a total length of the first tube assembly 23 and the second tube assembly 25 is reduced, which facilitates surgical operations. The fixation base 27 is fixed to the second sleeving end 253, and the gas cell 29 is sleeved to the fixation base 27.

As shown in FIGS. 2, 3, 3A, and 3B, the fixation base 27 is fixed to the second sleeving end 253, and the fixation base 27 comprises a passage 271, an inner wall 273, a guiding groove 275, and a key groove 277. The passage 271 penetrates through the fixation base 27 and is usually located at a center of the fixation base 27. The inner wall 273 extends from an inner surface of the fixation base 27 towards the passage 271 and forms a convex with an arc shape. The guiding groove 275 communicates the passage 271 and is adjacent to the inner wall 273. In the embodiment, as shown in FIG. 3, the fixation base 27 comprises, but is not limited to, two inner walls 273 and two guiding grooves 275 being adjacent to each other. The key groove 277 is on the inner wall 273 and communicates with the guiding groove 275. A width of an end of the key groove 277 away from the guiding groove 275 is less than that of an end of the key groove 277 close to the guiding groove 275. That is to say, the inner wall 273 is convex towards the end of the key groove 277 away from the guiding groove 275 and forms a block 2731. In some embodiments, the guiding groove 275 is deeper than the key groove 277.

As shown in FIG. 3A, while the bump 131 of the puncturing device 10 is entered into the fixation base 27 through the guiding groove 275, the puncturing device 10 is free to be withdrawn from or inserted into the fixation base 27. As shown in FIG. 3B, while the puncturing device 10 is rotated, the bump 131 is entered into the key groove 277 through the guiding groove 275. The bump 131 can slide continuously until the bump 131 contacts the block 2731 of the inner wall 273. The bump 131 cannot continue to slide while the bump 131 contacts the block 2731. In the meantime, the puncturing device 10 is secured to the fixation base 27, and the puncturing device 10 can drive the sleeving component 20 to move along the elongated direction of the puncturing device 13. After the puncturing device 10 is rotated to have the bump 131 be back to the guiding groove 275 from the key groove 277, the puncturing device 10 is free to be withdrawn from the sleeving component 20.

As shown in FIG. 4, a part of the puncturing portion 13 is in the assembling channel 2131, the first tube assembly 23, the second tube assembly 25, and the passage 271. The tip 133 is convex on the fixation base 27. After the puncturing device 10 is used to cut an opening on a human body 500, the sleeving component 20 can be moved with the puncturing device 10 along the elongated direction of the puncturing portion 13 under the circumstances that the puncturing device 10 is secured to the fixation base 27. Further, as shown in FIG. 5, while reaching a proper position, the gas cell 29 can be inflated through first gas valve 215. While the gas cell 29 is inflated, the sleeving component 20 can be secured to the human body 500. In the meantime, the puncturing device 10 can be rotated and withdrawn from the sleeving component 20.

FIG. 6 is a partially cross-sectional view of the sleeving component 20 of FIG. 5, which illustrates a flow of a gas. As shown in FIGS. 2, 4, 5, and 6, the first tube assembly 23 further comprises a first inner tube 241 and a first outer tube 243. The first tube assembly 23 is divided into a first wall region 23A and a second wall region 23B. The first outer tube 243 is around the first inner tube 241 in the first wall region 23A. The first outer tube 243 is not around the first inner tube 241 in the second wall region 23B. The second tube assembly 25 comprises a second inner tube 261 and a second outer tube 263. The second tube assembly 25 is divided into a third wall region 25A and a fourth wall region 25B. The second outer tube 263 is around the first outer tube 243 in the third wall region 25A. The second outer tube 263 is around the second inner tube 261 in the fourth wall region 25B. The first opening 2331 is on a wall of the first outer tube 243. The fixation base 27 further comprises a gas outlet 279. In the embodiment, a gas channel is formed by a communication between the first inner tube 241 and the first outer tube 243, a communication between the first opening 2331, the first outer tube 243, and the second outer tube 263, and a communication between the second outer tube 263 and the second inner tube 261, and by the gas outlet 279. After gas flows through the first gas valve 25, the gas flows along the gas channel and finally flows into the gas cell 29 through the gas outlet 279 to inflate the gas cell 29. As a result, as shown in FIG. 5, the sleeving component 20 can be secured to the human body 500.

Referring to FIG. 7, while the trocar 1 has been positioned, the gas cell 29 is inflated to have the sleeving component 20 secured to the human body 500. While the puncturing device 10 is withdrawn from the sleeving component 20, the handle 211 can be pushed to have the first tube assembly 23 received in the second tube assembly 25. The total length of the portion of the sleeving component 20 outside the human body 500 can be reduced. While the sleeving component 20 is retracted, the second tube assembly 25 is moved towards the gas pressure base 21 relative to the first tube assembly 23, and the first tube assembly 23 is retracted in the second tube assembly 25.

Specifically, referring to FIG. 2, FIG. 4, and FIG. 7, the trocar 1 further comprises a gas tight assembly 30. The gas tight assembly 30 is disposed on a sleeving area of the first tube assembly 23 and the second tube assembly 25. The gas tight assembly 30 comprises a blocking component 31 and a gas tight tube 33. The blocking component 31 is assembled to the first tube assembly 23 and is adjacent to the first sleeving end 233. The gas tight tube 33 is sleeved to the sleeving area of the first tube assembly 23 and the second tube assembly 25. The gas tight tube 33 covers the blocking component 31. As a result, gas wouldn't leak from a gap of the sleeving area.

As shown in FIG. 4 to FIG. 6, while the sleeving component 20 is extruded, the second tube assembly 25 is moved away from the gas pressure base 21 relative to the first tube assembly 23 until the blocking component 31 contacts the second tube assembly 25. In particular, after the blocking component 31 contacts a wall of the second outer tube 263, the second tube assembly 25 wouldn't be moved away from the gas pressure base 21 any further. As shown in FIG. 7, while the sleeving component 20 is retracted from an extruded state, the second tube assembly 25 is moved towards the gas pressure base 21 relative to the first tube assembly 23, and the first tube assembly 23 is being retracted in the second tube assembly 25 until the gas tight assembly 30 contacts the connecting portion 213.

Referring to FIGS. 2 and 4-7, the gas tight assembly 30 further comprises a gas tight ring 35. The gas tight ring 35 is sleeved to a portion of the first tube assembly 23 and contacts the blocking component 31. The gas tight ring 35 is covered by the gas tight tube 33. As a result, a gas tight effect can be achieved. In addition, the blocking component 31 can be a securing component with a screw type, which makes a connection more securely to avoid unintentional detaching while the first tube assembly 23 is received in the second tube assembly 25.

Referring to FIGS. 2 and 4-7, the gas pressure bas 21 further comprises a second gas valve 217. While the puncturing device 10 is withdrawn from the sleeving component 20, gas can be inflated into the human body 500 by the second gas valve 217 through the first tube assembly 23 and the second tube assembly 25 in which the puncturing device 10 is previously installed. In such manner, a tissue of the human body 500 can be partially inflated to facilitate insertion of the medical equipment such as an endoscope, an optical fiber, or a laser tool, observation, and surgical operation. In particular, the second gas valve 217 may be a switchable gas valve connected to an external inflating device for inflation. In addition, after an operation is accomplished, the first gas valve 215 can be turned on to have the gas cell 29 deflated, such that the sleeving component 20 can be withdrawn from the human body.

According to the trocar of the embodiments of the instant disclosure, the puncturing device can be secured to the fixation base of the sleeving component by the bump and the key groove. Therefore, the puncturing device can be moved with the sleeving component along the axial direction synchronously so as to be adjusted to a proper position immediately, which can avoid unnecessary damage and prevent wounds from being enlarged by unintentional contact. Patient can have less pain and less uncomfortable feeling. In addition, the first tube assembly and the second tube assembly are sleeved to each other, and the first tube assembly can be received in the second tube assembly such that the length of the sleeving component can be adjusted. A length of a portion of the sleeving component outside a human body can be shorten, which is convenient to medical staff for performing an operation.

While the instant disclosure has been described by way of example and in terms of the preferred embodiments, it is to be understood that the instant disclosure needs not be limited to the disclosed embodiments. For anyone skilled in the art, various modifications and improvements within the spirit of the instant disclosure are covered under the scope of the instant disclosure. The covered scope of the instant disclosure is based on the appended claims.

What is claimed is:

1. A trocar, comprising:
   a puncturing device comprising a base and a puncturing portion, the puncturing portion extending along a direction perpendicular to the base, the puncturing portion comprising a bump and a tip, the tip being on an end of the puncturing portion opposite to the base, the bump extending from an outer surface of the puncturing portion radially; and
   a sleeving component comprising:
   a gas pressure base comprising a handle, a connecting portion, and a first gas valve, the handle comprising an opening, the puncturing portion being inserted into the opening, the base contacting the handle, the connecting portion extending from the handle and comprising an assembling channel, the assembling channel communicating with the opening, the first gas valve being connected with the connecting portion and communicating with the assembling channel;
   a first tube assembly comprising a first assembling end and a first sleeving end, the first assembling end being assembled into the assembling channel, the first assembling end corresponding to the first gas valve, a wall of the first sleeving end comprising at least one first opening;
   a second tube assembly comprising a second assembling end and a second sleeving end, the second assembling end being adjustably sleeved to the first sleeving end, wherein the second tube assembly is retractable relative to the first tube assembly to have the first tube assembly received in the second tube assembly;
   a fixation base fixed to the second sleeving end and comprising a passage, an inner wall, a guiding groove, a key groove, and a gas outlet, the passage penetrating through the fixation base, the inner wall extending from an inner surface of the fixation base towards the passage, the guiding groove communicating with the passage and being adjacent to the inner wall, the key groove being on the inner wall and communicating with the guiding groove, a width of an end of the key groove away from the guiding groove being less than that of an end of the key groove close to the guiding groove, the gas outlet being on a surface of the fixation base, a portion of the puncturing portion being in the assembling channel, the first tube assembly, the second tube assembly, and the passage, the tip being convex on the fixation base; and
   a gas cell sleeved to the fixation base and corresponding to the gas outlet,
   wherein while the bump of the puncturing device is entered into the key groove through the guiding groove, and the puncturing device is rotated to have the bump slide along the key groove until the bump contacts the inner wall to have the puncturing device secured to the fixation base, the puncturing device drives the sleeving component to move along an elongated direction of the puncturing device.

2. The trocar of claim 1, wherein the first tube assembly further comprises a first inner tube and a first outer tube, the first tube assembly is divided into a first wall region and a second wall region, the first outer tube is around the first inner tube in the first wall region, and the first outer tube is not around the first inner tube in the second wall region, wherein the second tube assembly comprises a second inner tube and a second outer tube, the second tube assembly is divided into a third wall region and a fourth wall region, the second outer tube is around the first outer tube in the third wall region, the second outer tube is around the second inner tube in the fourth wall region, and the first opening is on a wall of the first outer tube.

3. The trocar of claim 2, wherein a gas channel is formed by a communication between the first inner tube and the first outer tube, a communication between the first opening, the first outer tube, and the second outer tube, and a communication between the second outer tube and the second inner tube, and by the gas outlet, wherein while a gas flows into the first gas valve, the gas flows along the gas channel and into the gas cell through the gas outlet.

4. The trocar of claim 1, further comprising a gas tight assembly, wherein the gas tight assembly is disposed on a portion of the first tube assembly and a portion of the second tube assembly, and the gas tight assembly seals a sleeving area of the first tube assembly and the second tube assembly.

5. The trocar of claim 4, wherein the gas tight assembly comprises a blocking component and a gas tight tube, the blocking component is assembled to the first tube assembly and is adjacent to the first sleeving end, the gas tight tube is sleeved to the sleeving area of the first tube assembly and the second tube assembly, and the gas tight tube covers the blocking component.

6. The trocar of claim 5, wherein the gas tight assembly further comprises a gas tight ring, the gas tight ring is sleeved to a portion of the first tube assembly and contacts the blocking component, and the gas tight ring is covered by the gas tight tube.

7. The trocar of claim 5, wherein while the sleeving component is extruded, the second tube assembly is moved away from the gas pressure base relative to the first tube assembly until the blocking component contacts the second tube assembly.

8. The trocar of claim 4, wherein while the sleeving component is retracted, the second tube assembly is moved towards the gas pressure base relative to the first tube assembly, and the first tube assembly is retracted in the second tube assembly until the gas tight assembly contacts the connecting portion.

9. The trocar of claim 4, wherein the gas tight assembly further comprises a securing component, and the securing component is assembled to the first sleeving end and contacts an inner surface of the second inner tube.

10. The trocar of claim 1, wherein while the bump is moved back to the guiding groove from the key groove, the puncturing device is free to be withdrawn from the sleeving component.

\* \* \* \* \*